United States Patent [19]

Hsu et al.

[11] Patent Number: 4,469,883
[45] Date of Patent: Sep. 4, 1984

[54] PALLADIUM CATALYZED OXY-ACETYLATION OF PHENYL ACETATE TO META-ACETOXYACETOPHENONE

[75] Inventors: Chao-Yang Hsu, Media; James E. Lyons, Wallingford, both of Pa.

[73] Assignee: Sun Tech, Inc., Philadelphia, Pa.

[21] Appl. No.: 262,158

[22] Filed: May 11, 1981

Related U.S. Application Data

[63] Continuation-in-part of Ser. No. 137,708, Apr. 7, 1980, abandoned.

[51] Int. Cl.³ .............................................. C07C 67/00
[52] U.S. Cl. .................................. 560/131; 568/319; 568/337
[58] Field of Search ................ 560/130, 131; 568/331

[56] References Cited

U.S. PATENT DOCUMENTS 3,725,462  4/1973  Boldt et al. ..................... 560/131
3,772,383  11/1973  Kominami et al. ............... 560/131

OTHER PUBLICATIONS

Eberson et al., Acta Chemica Scandinavica B30, pp. 361–364, (1976).

Primary Examiner—J. E. Evans
Attorney, Agent, or Firm—J. Edward Hess; Donald R. Johnson; Patrick C. Baker

[57] ABSTRACT

Acetoxyacetophenone is the predominant product when phenyl acetate, acetic acid and acetic anhydride are reacted in the presence of palladium and a gas mixture containing an inert gas and more than 13 vol. % oxygen. Secondary products are hydroxyacetophenone and phenylene diacetates. The meta isomers predominate when a metal acetate is present in the reaction mixture. Mineral acids cause shift to ortho isomers.

10 Claims, 2 Drawing Figures

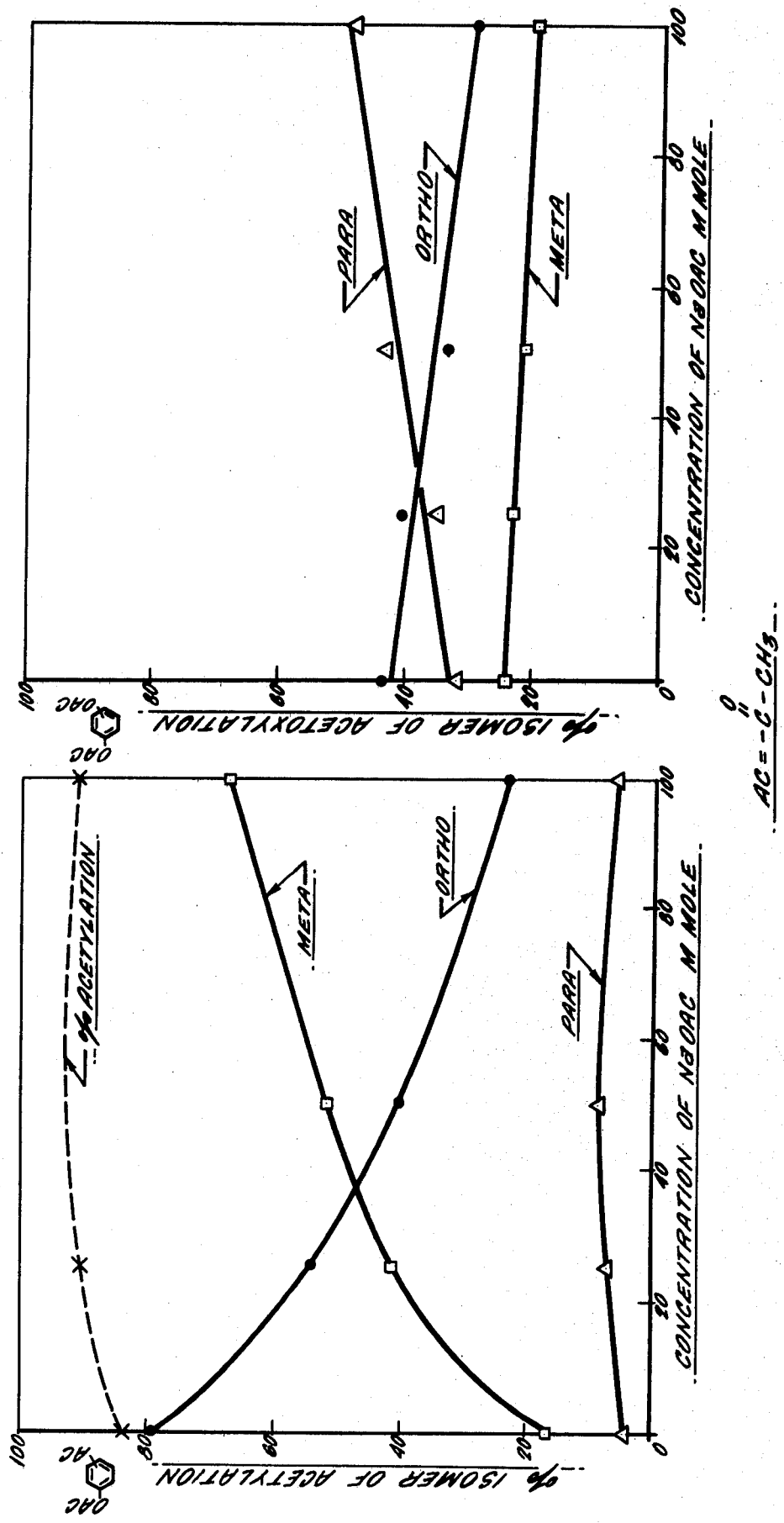
Fig. 1. Effect of concentration of metal acetate on product and isomer distribution.

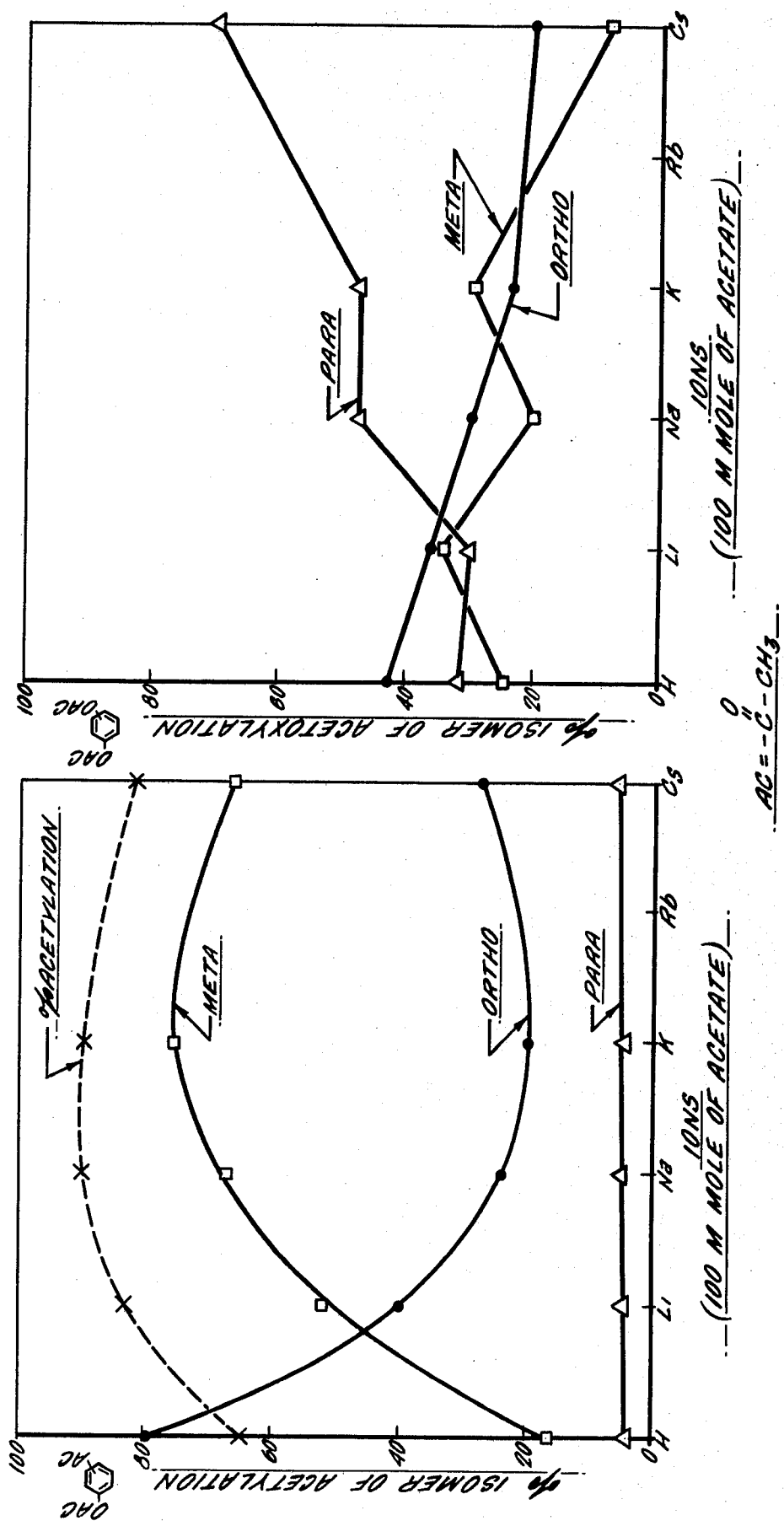

PALLADIUM CATALYZED OXY-ACETYLATION OF PHENYL ACETATE TO META-ACETOXYACETOPHENONE

RELATED APPLICATIONS

This application is a continuation-in-part of U.S. application Ser. No. 137,708 filed Apr. 7, 1980 and abandoned as of the filing of this application.

The subject matter of this application is related to U.S. Application Ser. No. 137,707, filed Apr. 7, 1980, and now abandoned, and to a copending continuation-in-part application thereof, Ser. No. 262,157, filed simultaneously with this application, entitled "Selective Production of Phenylene Diacetate," now U.S. Pat. No. 4,332,963 issued June 1, 1982.

BACKGROUND OF THE INVENTION

This invention relates to a process for the preparation of various acetoxyacetophenones. More particularly the invention relates to the conversion of phenyl acetate to acetoxyacetophenones by a palladium catalyst in the presence of oxygen, acetic anhydride and acetic acid at elevated temperatures and pressures. The presence of a metal acetate or a mineral acid, in addition to the aforementioned materials, can influence the product distribution. Acetoxyacetophenones are used in pharmaceutical formulations. Preparation of phenyl acetate is disclosed in U.S. Pat. No. 4,156,783.

In Preparative Organic Chemistry, edited by G. Hilgetag and A. Martini, John Wiley & Sons, 1972, pages 934–935, it is disclosed that acetylation of aromatic compounds containing electron-donating substituents, and phenyl acetate is such an aromatic compound, give ortho- and para-compounds almost exclusively. Thus it is surprising that applicants' method can result in favoring meta isomers.

The acetoxylation of acetophenone using Pd(II) and potassium peroxydisulfate yields acetoxy derivatives having an isomer distribution of 1% ortho, 77% meta, and 22% para according to Acta Chemica Scandinavia B30 (1976) 361–364, Eberson et al.

SUMMARY

The process of this invention comprises reacting phenyl acetate, acetic acid and acetic anhydride in the presence of (a) a gas mixture containing oxygen and (b) a palladium catalyst, at an elevated temperature and pressure to yield acetoxyacetophenones in accordance with the following reaction:

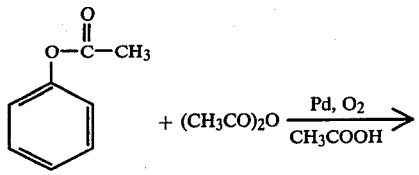

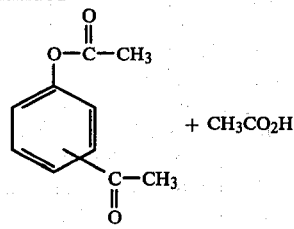

Since either acetic acid or acetic anhydride, or both, can be the source of the acetyl group,

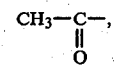

which bonds to the phenyl acetate, the foregoing reaction scheme is merely representative of the possible reactions which may occur.

The presence in the reaction mixture of optional metal acetate or a mineral acid, in addition to those materials already mentioned, influences the distribution of the products and isomers. In addition to acetoxyacetophenones, the foregoing reaction is accompanied by the production of hydroxyacetophenones and phenylene diacetates.

DRAWING

The accompanying Figures demonstrate the effect of the concentration and kind of metal ion on product distribution. FIG. I shows the effect of various concentrations of sodium acetate on product distribution; the graph on the left shows the product distribution of the acetoxyacetophenones whereas the graph on the right shows the product distribution of the phenylene diacetates. FIG. II shows the effect of various metal ions on the product distribution; the graph on the left side shows the product distribution of the acetoxyacetophenones whereas the graph on the right shows the product distribution of the phenylene diacetates.

DETAILED DESCRIPTION

"Oxy-acetylation" as used in this specification refers to the palladium catalyzed addition of the acetyl group,

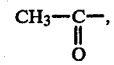

to phenyl acetate in the presence of substantial amounts of oxygen under conditions in which essentially no acetylation occurs in the absence of oxygen.

The process of this invention is conveniently carried out in liquid phase under oxy-acetylation conditions, that is, conditions which favor the formation of acetoxyacetophenones. These conditions include elevated temperatures and pressures, and oxygen content. Temperatures of from about 125° C. to about 250° C. are preferred with about 150° C. to about 200° C. more preferred. Reaction pressures of from about 100 psig up to about 1500 psig are preferred. The reaction time may vary over a wide range, depending in part on the operating conditions, including, for example, catalyst, relative concentrations of materials, and the temperature and pressure. The process can also be carried out in a batch, continuous, or semi-continuous system.

The amount of acetic acid is not critical. A preferred range is from about 0.2 to about 5.0 moles per mole of phenyl acetate.

The acetic anhydride desirably should be present in the amount of about 0.1 to about 3 times by weight of the amount of phenyl acetate, with 0.3 to 1.5 preferred. The molar ratio of palladium catalyst to phenyl acetate is in the range of from about 0.0001 to about 1 with 0.001 to 0.5 preferred.

The amount of oxygen is an oxy-acetylation amount, that is, an amount which favors the formation of acetoxyacetophenones rather that the phenylene diacetates of the copending application referred to above. Generally the oxygen is used in admixture with an inert gas such as nitrogen. The oxygen content of the gas mixture should be maintained at a concentration above 13 volume %, preferably from about 15 to about 50 volume % or more. At 13 volume % or below, acetoxylation is favored, as described in the aforementioned copending application.

The palladium catalyst desirably is palladium on alumina. Other palladium catalysts, e.g., palladium acetate, and palladium having other supports, e.g., carbon, and silica, which would result in an effective reaction mixture can be used.

As heretofore stated, the presence of an optional metal acetate or mineral acid can influence the distribution of the products. The metal acetates include the group IA metal acetates, i.e., Li, Na, K, Rb and Cs, which are preferred. When the group IA metal acetate is admixed with the reaction mixture the isomer distribution shifts from predominantly the ortho-acetoxyacetophenone to predominantly the meta-acetoxyacetophenone. This is shown graphically in FIG. II. The metal acetate desirably should be present in the amount of about 1 to 200 times the amount of catalyst.

The mineral acids include, for example, $HNO_3$, $H_2SO_4$, $H_3PO_4$ and the like. As shown in the examples, when nitric acid was added to the reaction mixture (not including any metal acetates) the resulting product was mainly ortho-acetoxyacetophenone. The mineral acid desirably should be present in the amount of about 0.5 to 5 moles of acid per mole of catalyst.

Generally, applicants' method results in converting phenyl cetate into a major amount of acetoxyacetophenones and hydroxyacetophenones. The isomer distribution as to the acetoxyacetophenones and hydroxyacetophenones can vary substantially depending, in part, on the concentration of and particular metal acetate or mineral acid used. Other products include phenylene diacetate, catechol, hydroquinone, resorcinol and phenol in various minor amounts.

The following examples are illustrative of various embodiments of the invention described herein.

EXAMPLES

One demonstration of the process for oxy-acetylation of phenyl acetate involved the following. To a stirred stainless steel autoclave were charged acetic acid, 4192 mmoles; acetic anhydride, 508 mmoles; phenylacetate, 946 mmoles; and 5% palladium on alumina (407 mmoles Pd). The reaction mixture was heated to 175° C. underi nitrogen (@500 psig) and then synthetic air (21% $O_2$ and 79% $N_2$) was passed through the mixture for 1 hour at the rate of one liter per minute (@500 psig). No metal acetate was used in this demonstration. A sample of the reaction mixture, after separation from the catalyst, was quantitatively analyzed by gas chromatography. The analytical results are tabulated in Table 1.

TABLE I

| | Yields & Isomer Distribution | | | | |
|---|---|---|---|---|---|
| | Yields | | Isomers (%) | | |
| Product* | mmoles | % | Ortho | Meta | Para |
| $C_6H_4(OAc)_2$ | 9.9 | 10 | 35.9 | 29.2 | 34.9 |
| $C_6H_4(OAc)(Ac)$ | 59.8 | 60 | 81.8 | 15.3 | 2.9 |
| $C_6H_4(OH)(Ac)$ | 16.3 | 16 | ≧98 | — | — |
| $C_6H_4(OH)_2$ | 13.5 | 14 | 1.2 | 17.6 | 81.2 |

*Ac = $CH_3-\underset{\underset{O}{\|}}{C}-$

The results in Table I indicate that about 60% of the product yield was acetoxyacetophenone with about 82% selectivity to the ortho isomer.

A number of runs were made to determine the effect of the metal acetate used and the amount of the acetate. These runs were made in the following manner. To a 300 ml rocker bomb were charged the following materials: acetic acid, 1040 mmoles; acetic anhydride, 127 mmoles; phenyl acetate 235 mmoles; 5% palladium on alumina (1.175 mmoles Pd) and various amounts and kinds of metal acetate. The pressure was 300 psig of synthetic air containing 21% $O_2$ and 79% $N_2$ and temperature was 175° C. The results are shown in FIGS. I and II. The data obtained for FIG. I was obtained using various concentrations (as shown in the graph) of sodium acetate. The data for FIG. II was obtained using 100 mmoles of various other metal acetates.

The curves (left side graph) shown in FIG. I demonstrate that as the concentration of the metal acetate (sodium acetate) increases, the isomer distribution for acetylation shifts from predominantly ortho-acetoxyacetophenone to predominantly meta-acetoxacetophenone. However, no such predominant shift is seen from the curves (right side graph) for the acetoxylation isomers. Also shown in FIG. I is the % of acetylation, i.e., the amount of acetylation products formed divided by the total amount of acetylation products plus acetoxylation products (times 100), that occurs under the described conditions. The % acetylation curve indicates that at least about 84% of the product formed is as a result of acetylation.

The curves (left side graph) shown in FIG. II demonstrate that as the atomic number of the metal ion increases the isomer distribution for acetylation shifts from predominantly ortho-acetoxyacetophenone to predominantly meta-acetoxyacetophenone. The isomer distribution for the acetoxylation products shifts from an ortho favored distribution to a predominantly para-isomer favored distribution as can be seen from the curves (right side) of FIG. II. Also shown on FIG. II is the % of acetylation that occurs under the described conditions. The % acetylation curve indicates that at least about 65% of the product formed is as a result of acetylation.

Table II shows representative yields and isomer distribution when potassium acetate (100 mmole) was used in place of the sodium acetate in a procedure otherwise substantially identical to that described above.

TABLE II

| Effect of Potassium Acetate on Yields and Isomer Distribution | | | | | |
|---|---|---|---|---|---|
| | Yields | | Isomers (%) | | |
| Product* | mmoles | % | Ortho | Meta | Para |
| $C_6H_4(OAc)_2$ | 1.2 | 9.5 | 23.0 | 29.6 | 47.4 |
| $C_6H_4(OAc)(Ac)$ | 8.9 | 70.6 | 19.7 | 76.0 | 4.3 |
| $C_6H_4(OH)(Ac)$ | 2.5 | 19.8 | ≧99 | — | — |
| $C_6H_4(OH)_2$ | trace | — | — | — | — |

*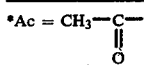

When the metal acetate was omitted and nitric acid was used in a 1:1 ratio to the palladium catalyst in an otherwise substantially identical procedure, the isomer distribution was as shown in Table III.

TABLE III

| Effect of Nitric Acid on Yields and Isomer Distribution | | | | | |
|---|---|---|---|---|---|
| | Yields | | Isomers (%) | | |
| Product* | mmoles | % | Ortho | Meta | Para |
| $C_6H_4(OAc)_2$ | 1.4 | 13.3 | 37 | 21 | 42 |
| $C_6H_4(OAc)(Ac)$ | 6.7 | 64.0 | 94 | 6 | trace |
| $C_6H_4(OH)(Ac)$ | 1.0 | 9.4 | 100 | — | — |
| $C_6H_4(OH)_2$ | trace | — | — | — | — |
| $C_6H_5OH$ | 1.4 | 13.3 | — | — | — |

*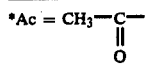

The acetoxyacetophenones, phenylene diacetates and other products can be separated from the reaction mixture and each other by known methods. Also, the isomers of the different products can be separated from each other by known methods, for example, by a combination of distillation and crystallization.

We claim:

1. A process for the acetylation of phenyl acetate, which comprises reacting, at elevated temperature and pressure and in the presence of a palladium catalyst and a gas mixture comprising an inert gas and more than 13 vol. % oxygen, a reaction mixture comprising phenyl acetate, acetic acid and acetic anhydride, whereby acetoxyacetophenone is produced as the predominant product.

2. Process according to claim 1 wherein there is additionally present a group 1A metal acetate in molar amount of about 1 to 200 times the amount of catalyst whereby the predominant product is meta-a-cetoxyacetophenone.

3. Process according to claim 1 wherein there is additionally present a mineral acid in an amount of about 0.5 to 5 moles per mole of catalyst whereby the predominant product is ortho-acetoxyacetophenone.

4. Process according to claim 1 wherein the pressure ranges up to about 1500 psig.

5. Process according to claim 1, 2 or 3 wherein the 4 wherein the temperature is from about 125° C. to about 250° C.

6. Process according to claim 1 wherein the amount of acetic anhydride is from about 0.1 to about 3 times by weight of the phenyl acetate.

7. Process according to claim 1 wherein the molar ratio of palladium catalyst to phenyl acetate is from about 0.0001 to about 1.

8. Process according to claim 1 wherein the amount of oxygen in the gas mixture is about 15–50 vol. %.

9. Process according to claim 1 wherein the amount of oxygen in the gas mixture is about 21 vol. %.

10. Process according to claim 1 wherein the amount of acetic anhydride is from about 0.1 to about 3 times by weight of the amount of phenyl acetate, the ratio of palladium catalyst to phenyl acetate is from about 0.0001 to about 1, the temperature is from about 125° C. to about 250° C., and the amount of oxygen in the gas mixture is about 15–50 vol. %.

* * * * *